United States Patent [19]

O'Reilly et al.

[11] Patent Number: 6,140,554
[45] Date of Patent: Oct. 31, 2000

[54] SPECIFICITY OF GENE EXPRESSION

[75] Inventors: David O'Reilly, Southampton; Christopher John Robert Thomas, Cambridge, both of United Kingdom

[73] Assignee: Advanced Technologies (Cambridge) Limited, London, United Kingdom

[21] Appl. No.: 09/049,475

[22] Filed: Mar. 27, 1998

[30] Foreign Application Priority Data

Mar. 27, 1997 [GB] United Kingdom .................. 9706381

[51] Int. Cl.⁷ ............................. C12N 5/04; C12N 15/82; C12N 15/90; C12N 15/09; A01H 5/00
[52] U.S. Cl. .................. 800/287; 435/69.1; 435/320.1; 435/419; 435/430; 435/468; 800/286; 800/298
[58] Field of Search ............................ 435/69.1, 320.1, 435/410, 419, 468; 800/278, 285, 286, 287, 288, 295, 298

[56] References Cited

FOREIGN PATENT DOCUMENTS

WO 89/10396  11/1989  WIPO ............................... C12N 5/00
WO 92/21757  12/1992  WIPO ............................. C12N 15/29
WO 93/10251  5/1993   WIPO ............................. C12N 15/82

OTHER PUBLICATIONS

Kneissl et al, Plant Physiol., vol. 112, pp. 537–547, 1996.
van der Krol, Nature, vol. 333, jpages 866–869, 1988.
Rochester et al, EMBO J., vol. 5, pp. 451–458, 1986.
Conkling et al., 1990, "Isolation of transcriptionally regulated root-specific genes from tobacco", *Plant Physiol.* 93:1203–1211.
Opperman et al., 1994, "Root–knot nematode–directed expression of a plant root–specific gene", *Science* 263:221–223.

*Primary Examiner*—Elizabeth F. McElwain
*Assistant Examiner*—Ashwin D. Mehta
*Attorney, Agent, or Firm*—Pennie & Edmonds LLP

[57] ABSTRACT

This invention seeks to improve the specificity of gene expression by targeting a specific expression site of a target gene. There is thus provided a chimaeric gene which comprises a promoter which expresses in more than one region of the organism to be affected. The promoter is linked to an agent which affects the functioning of an endogenous gene in the plant which is also expressed in more than one region of the plant. The promoter and agent are selected so that there is an overlap in their expression sites at one or more desired locations. This overlap site(s) gives increased specificity and targeting of gene expression.

19 Claims, 4 Drawing Sheets

SPECIFICITY OF GENE EXPRESSION

This invention relates to a method for increasing the specificity of gene expression. In particular, the invention relates to the use of a chimaeric gene to generate a highly specific targeting effect as a mode of providing, for example but not exclusively, a targeted resistance to disease-causing agents in plants.

Figure 1:
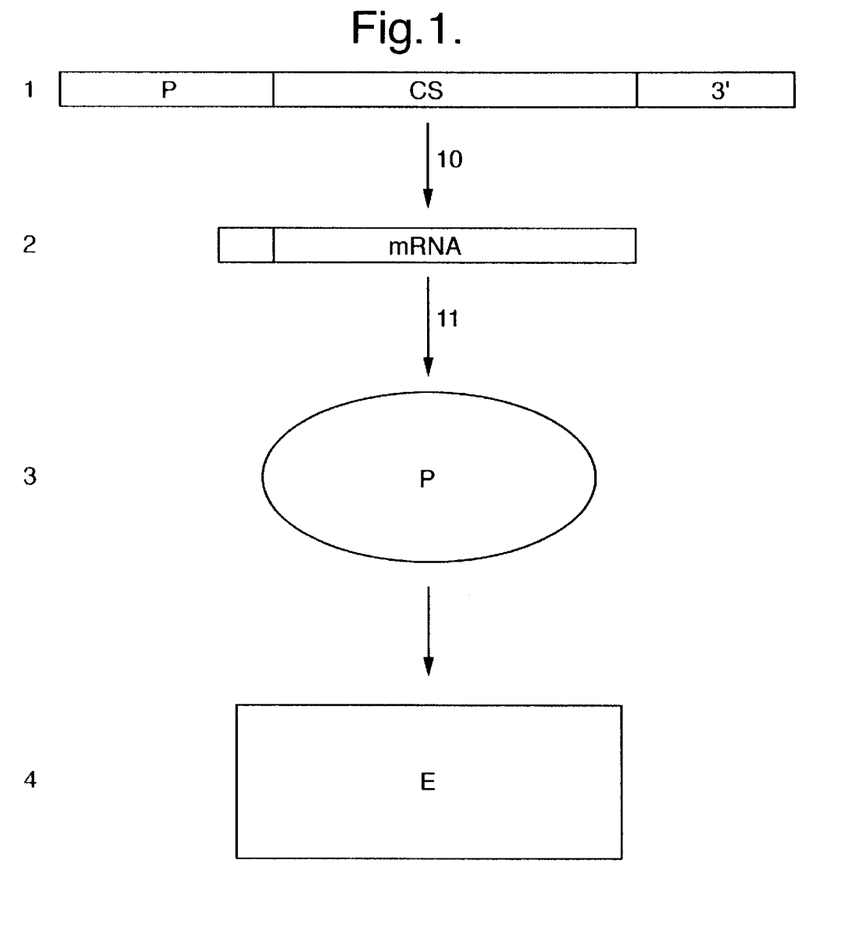
FIG. 1 shows a diagrammatic representation of the expression of a gene in a cell

For the purpose of this invention it is useful to describe in a simplified manner how a gene is constructed and how it functions (see FIG. 1 which shows the structure of a gene, which gene may also be a chimaeric gene). A gene can be considered to consist of three components (the numbers refer to the numbers in FIG. 1); 1. a promoter (P) which determines when and where a coding sequence is transcribed, a coding sequence (CS) for the production of a protein and a 3' regulatory sequence (3') that can sometimes also affect the transcription of the coding sequence. The 3' regulatory sequence is commonly known as a terminator. 2. A gene is expressed when the promoter permits the transcription and processing (10) of a working copy of the coding sequence to produce a messenger RNA (mRNA). 3. The mRNA is then translated (11) to give a protein product. 4. The protein product can then interact with a substrate or another protein or a regulatory sequence to cause an effect (E).

However, it should be noted that regulation of the expression of a gene can be affected at each stage of the expression process described above. Factors can act on the promoter, on the transcription machinery to produce the mRNA and on processes that modify the mRNA or affect its stability. Factors can also act on the translation of the protein and on the turnover of the protein within the cell. Other factors can influence how the protein interacts with other components and achieves its effect.

To explain the inventive concept, consider the following genes, gene 1 and gene 2 in a plant. Gene 1 is active in tissues A and B of a plant, whilst gene 2 is active in regions B and C of a plant. The activities of the two genes overlap in region B and this can be described visually as in FIG. 2, which is in the form of a Venn diagram. From this Figure it is apparent that the site of joint expression is more limited or, in other words, more specific than the sites of expression of either gene on their own.

Thus in this invention, in respect of plants, the chimaeric gene contains a promoter which expresses in more than one region of the plant. The promoter is linked to an agent. The agent will affect the functioning of an endogenous gene which is also expressed in more than one region of the plant. The areas in which the promoter and the endogenous gene to be affected are active are not identical but they do overlap at one or more desired locations. When the chimaeric gene is transferred into a plant, the agent will only have an effect on the target endogenous gene at the location(s) of overlap.

There are several ways to exemplify the invention, of which increased tolerance or resistance to plant parasitic nematodes is a practical example. Although we have used cell disruption and male sterility as examples, the system can also be used for the enhancement of a gene at a particular site.

Several different mechanisms have been proposed to obtain cell specific disruption. The simplest method utilises a chimaeric gene comprising a promoter specific to the targeted tissue linked to a disruptive system. Even specific promoters, however, may express to a lesser degree in tissues other than those targeted, which is sometimes undesirable.

Other applications have attempted to circumvent this problem by utilising two constructs, the first construct containing a chimaeric gene comprising a tissue specific promoter linked to a cell necrosis system (e.g. barnase) and the second construct containing a chimaeric gene comprising a promoter active in regions other than the one targeted, the promoter being linked to a protectant (e.g. barstar) which inactivates the necrosis system. The necrosis in tissues other than the one desired is therefore suppressed by the protectant (see International Patent Application Nos. WO92/21757 (Plant Genetic Systems N.V.) and WO 93/10251 (Mogen International N.V.)).

This invention can provide, for example, a highly specific cell disruption system using a single construct. Other cell regulation systems to which the invention is applicable will be known to the skilled man.

SUMMARY OF THE INVENTION

It is an object of the invention to provide a site specific expression system or targeting system which is generally applicable to any organism which has genes expressed in different regions but where their sphere of expression overlaps.

It is also an object of the invention to achieve increased specificity using only one construct comprising a chimaeric gene comprising two or more nucleic acid sequences, which construct is designed to interact with an endogenous gene in an organism.

The present invention provides a method of improving the specificity of gene regulation in a transformed organism, the method comprising the steps of identifying an endogenous target gene in an organism, determining the location of more than one expression sites of the target gene, creating a chimaeric gene comprising a promoter which causes gene expression at at least two expression sites in an organism, including expression at one of the expression sites of the target gene, and an agent being a nucleic acid sequence which regulates expression of the target gene or a product thereof, stably incorporating the chimaeric gene into a cell of the organism by genetic transformation, and regenerating an organism from the transformed cell, which transformed organism contains the chimaeric gene, the expression of which gene in the organism causes the target gene or a product thereof to be regulated at at least one specific expression site in the transformed organism or progeny thereof.

Preferably the nucleic acid sequence is a coding or a non-coding sequence.

Preferably the expression of the target gene can be up regulated or down regulated.

Preferably the organism is a plant, whereby the transformed plant or propagules thereof contain the chimaeric gene.

The mechanism whereby the agent acts on a gene could belong to any one of the following. The list should not be considered to be exclusive.

1. antisense.
2. cosuppression.
3. inhibition or activation of the promoter of a target gene.
4. inhibition or activation of transcription.
5. alteration of messenger RNA stability or degradation of mRNA.
6. inhibition or activation of translation.
7. inhibition or activation of a protein 8. alteration of protein turnover.
9. acting as a cofactor.
10. alteration of protein-protein interactions.
11. alteration of the flux through a biochemical pathway.

Some examples of these mechanisms are discussed briefly below. It should be borne in mind that the particular mechanism to be selected to achieve gene regulation will also require a certain level of site specific expression in order to be effective in the inventive concept.

Down regulation may advantageously be achieved by the agent of the chimaeric gene being a nucleic acid sequence which is the antisense orientation of the whole or part of the promoter or a coding or non-coding sequence of the target gene. Alternatively, down regulation may be achieved by cosuppression of the promoter or coding or non-coding sequence of the target gene.

Up regulation of the target gene may be achieved, for example, by introducing an activator of the promoter of the target gene.

Combinations of these technologies may also be used.

Other suitable methods of regulating gene expression of the target gene will be known to those skilled in the art.

The agent of the chimaeric gene may comprise one or more nucleic acid sequences, each of which sequences, when expressed, carries out a particular function. There may thus be obtained specificity of expression of more than one endogenous gene using only one promoter.

A construct can contain two separate chimaeric genes as expression cassettes, each chimaeric gene comprising a promoter, a coding sequence for an agent and a terminator. Each chimaeric gene acts on a different endogenous gene, which gene may be expressed at the same target site or a different site. There is thus the possibility of knocking out or increasing several components or target genes in a sequence of events, such as a particular biosynthesis chain, over a period of time. In other words, a temporal chain of events can be effected. Alternatively, each chimaeric gene could be transferred into the organism in two separate constructs, each construct containing one expression cassette, i.e. one chimaeric gene.

The nucleic acid sequence may be a DNA sequence or an RNA sequence.

The promoter of the chimaeric gene may be expressed in more than one overlapping expression site of the endogenous gene.

Advantageously the promoter is a nematode-inducible promoter, such as the promoter known herein as the KNT1 promoter or the RB7 promoter. Other promoters which are caused to express by other agents acting on them at other attacked or growth sites may be utilised depending on the site specific expression regulation to be achieved.

Advantageously the nucleic acid sequence is the or a part of the antisense sequence of the RB7 or KNT1 promoter or coding sequence thereof.

Alternatively the nucleic acid sequence may be a ribozyme or a targeted RNase to degrade a messenger RNA in order to effect, for example, mechanism 5 of the list of mechanisms above. Also, specific RNA's can be stabilised or destabilised by specific nutrients, e.g. iron in the case of the mRNA for the cell surface protein receptor for transferring; or ligands, hormones and translation products, e.g. the effect of tubulin protein dimer on tubulin mRNA. Selection of nutrients, ligands, hormones or translation products expressed or required at certain locations is desirable for the inventive concept.

An example of an activator of transcription is the heat shock factor of Drosophila which encodes a protein free in the cell. Upon heat shock, the heat shock gene factor binds to the promoter of the heat shock protein HSP70 and leads to increased transcription. Heat shock proteins are found in bacteria, animals and plants. Activators suitable for use in the inventive concept which are site specific can be selected by the skilled man to achieve mechanism 4.

Suitable cofactors for effecting mechanism 9 in an organism include vitamins such as pantothenic acid and vitamin B6.

Finally, mechanism 10 could be effected by introducing, for example, the protein cAMP-dependent protein kinase into an organism. The cAMP-dependent protein kinase acts upon the the enzyme glycogen synthase by phosphorylating it. The glycogen synthase is turned into a less active form and glycogen synthesis is inhibited.

The invention may also utilise a number of constructs, each promoter-gene fragment of the chimaeric gene of each construct having an overlap at the same target expression site as each of the other promoter-gene fragments, so that there is provided multiple overlap at the selected single expression site to further enhance the specificity of the system. The other expression site of the chimaeric gene may be the same as or different from the other expression sites of the other promoter-gene fragments.

BRIEF DESCRIPTION OF THE FIGURES

In order that the invention may be easily understood and readily carried into effect, reference will now be made, by way of example, to the following figure and example in which.

Figure 2:
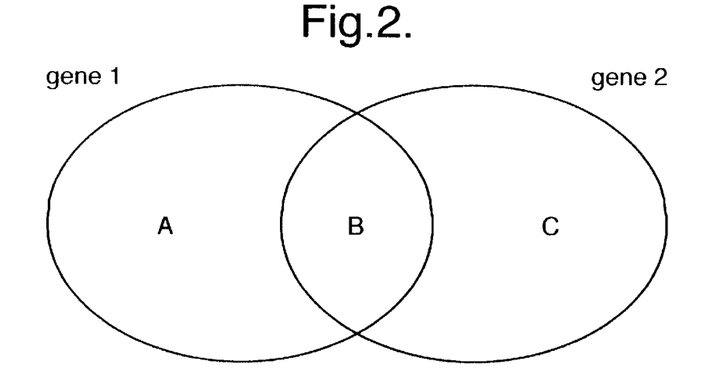
FIG. 2 shows the overlap of the expression sites of the two separate genes when they are in the same plant.

Cell specific disruption at site B in FIG. 2 can be achieved as follows. The promoter which regulates the specificity of expression from gene 1 can be linked to a region which will disrupt the activity of gene 2 in a construct. When the construct is introduced into plants, the agent disruptive of gene 2 will be expressed in regions A and B. There will be no effect at site A because gene 2 is not active here. There will be no effect at site C because the promoter of the construct is not active there and hence no disruptive agent for gene 2 is produced. There will be disruption of gene 2 at site B as the disruptive agent for gene 2 is present and gene 2 is also active.

DETAILED DESCRIPTION OF THE INVENTION

EXAMPLE 1

Engineering increased tolerance or resistance to plant parasitic nematodes using Venn constructs.

Plant parasitic nematodes such as the root knot nematodes and cyst nematodes cause 7 to 14% losses in crop yield world wide. The nematodes act by penetrating plant roots and generating unique feeding sites through which they derive their nutrients. The feeding sites are altered plant cells, either giant multinucleate cells in the case of root knot nematodes, or syncitia of several cells fused together in the case of cyst nematodes. The nematodes become sessile and are totally dependent on the feeding sites for nutrients. Our U.S. Pat. No. 5,589,622 describes a general way of making plants resistant by linking feeding cell specific promoters to cell death or cell disruption systems to disrupt the feeding cells. The feeding cells are impaired in their function so the nematode starves or has a reduced food supply and is unable or less able to grow and to produce offspring. This method is an example of the simplest method of cell specific disruption described above. Other patents which utilise this principle are those which create sterility in a plant, for example, International Patent Application No. WO 89/10396 (Plant Genetic Systems N.V.)

Promoter KNT1 which is expressed in feeding cells, root tips and to a lesser extent in other meristems was identified. Other workers have identified a gene, RB7 expressed in roots and giant cells (Conkling et al 1990, Opperman et al 1993). Our studies with the RB7 promoter linked to the marker gene GUS suggest that the RB7 gene is expressed in the body of the root and not at the root tip. A Venn construct containing the promoter to KNT1 linked to a partial anti-sense sequence of RB7 coding sequence and a nos terminator in a pBIN19 (Bevan, M. 1984) derived plant transformation vector containing *Agrobacterium tumefaciens* C58 was made. The construct was labelled pBIN05002 and was deposited by Advanced Technologies (Cambridge) Ltd of 210 Cambridge Science Park, Cambridge CB4 4WA, England under the Budapest Treaty on the International Recognition of the Deposit of Micro-organisms for the purposes of Patent Procedure at the National Collection of Industrial and Marine Bacteria (NCIMB), 23 St. Machar Street, Aberdeen, Scotland on Mar. 20th 1997 under accession number NCIMB 40871. Tobacco plants cv Heavy Western were transformed with this construct using Agrobacterium mediated plant transformation in accordance with the method of Horsch et al (1985).

Regenerated transgenic plants were transferred to the greenhouse. Transgenic plants and non-transgenic controls were each infected with about 100 individuals of the root knot nematode *Meloidogyne javanica*. Eight weeks after infection the number of visible root knots and their size was determined. During this period the initial inoculum had the opportunity to infect, mature and produce a second generation of nematodes which in turn could infect the plant roots and mature.

Eight of the lowest scoring transgenic pBIN05002 plants were grown to seed. Progeny from parent plants were again screened for increased tolerance or resistance to *M. javanica* as described above. In addition to the pBIN05002 plants, progeny from plants transformed with pBIN05101 containing the KNT1 promoter linked to the glucuronidase marker gene (GUS) (Jefferson, R. A. et al 1987) and progeny from untransformed plants were included as controls for comparison. pBIN05101 was also deposited at the NCIMB on Mar. 20th 1997 under accession number NCIMB 40870. Progeny from pBIN05002 plant line 32 showed a significant increase in the number of plants with low gall scores as shown in Table 1. The results are significant in a Chi square analysis.

TABLE 1

Number of plants in low and high gall score categories for untransformed control plants, control pBIN05101 plants and pBIN05002 test plants.

Low gall score = 0 to 50 galls per plant.
High gall score = 51 + galls per plant.

| Treatment | plants with low gall score | plants with high gall score |
| --- | --- | --- |
| Untransformed plants | 18 | 13 |
| pBIN05101 control plants | 13 | 17 |
| pBIN05002 line 32 test plants | 25 | 7 |

EXAMPLE 2

The overlap principle illustrated in the above example using a cell disruption system for increased specificity in nematode disruption can equally well be carried out in the flower of Arabidopsis, for example, or other plants to provide flowers with altered flower pattern or structure, for example, male sterility. This example utilises DNA sequences identified in Arabidopsis.

There are four elements of the flower (sepal, carpel, petal and stamen) which are postulated to be under the control of three genes (Coen, E. S. and Meyerowitz, E. M., 1991).

Altering the balance of these genes causes a variation in flower pattern. For example, both the gene agamous and apetala3 must be expressed in the same part of the flower to give rise to the male part of the plant, the stamen. Agamous is expressed both in the carpels and stamens, whilst apetala3 is expressed in both stamens and petals.

In order to make a construct following the overlap principle which is the subject of this invention, we require the promoter from one gene (e.g. agamous, active in carpels and stamens) linked to a disrupter of a second gene (e.g. apetala3, active in petals and stamens) to effect disruption in only the stamens.

A 435 basepair fragment of the agamous promoter was isolated from *Argabidopsis thaliana* DNA using the polymerase chain reaction with Taq and Taq-extender using the following two primers according to published procedures (Thomas, C., 1996):

```
Primer 1 (SEQ ID NO:1)

ATCGAAGCTT CTAAATGTAC TGAAAAGAAA CA

Primer 2 (SEQ ID NO:2)

ACTGGGATCC GAAAATGGAA GGTAAGGTTG TGC
```

Primers were based on the sequence given in the Genbank DNA sequence entry ATAGAMSG for the genomic agamous sequence. Primer 1 contains an added HindIII restriction site at its 5' end. Primer 2 contains an added BamHI restriction site at its 5' end.

The following primers were designed from the Genbank sequence entry ATHAPETALA in order to amplify out part of the apetala3 gene sequence:

```
Primer 3 (SEQ ID NO:3)
```

```
            -continued
ATCGGGATCC ATGGGCTCAC GGTTTTGTGT GA

Primer 4 (SEQ ID NO:4)

ATCGGAGCTC TTATTCAAGA AGATGGAAGG TAATGA
```

Primer 3 was specifically designed to begin amplification at position 992 of the published apetala3 sequence, which is a start codon in the wrong reading frame, to produce an active product and which avoids the initial part of the sequence that has strong homologies with other MADS box genes in the same gene family. Primer 3 also contained a one base pair change from the published sequence to remove an unwanted SacI restriction site. Primer 3 has a BamHI restriction site at its 5' end. Primer 4 has a SacI site at its 5' end. A 1586 bp fragment was amplified from Arabidopsis DNA using primers 3 & 4 using PCR.

The following cloning methods are familiar to any one skilled in the art and the results can be obtained by following the methods in Sambrook et al (1989). The agamous promoter fragment was ligated into a pBluescript derived vector (Stratagene Ltd., Cambridge, UK) as a HindIII-BamHI fragment. The altered apetala gene fragment was ligated downstream of the agamous promoter as a BamHI-SacI fragment in the same vector. The vector also contained a nos terminator sequence downstream of the altered apetala3 sequence as a SacI-EcoRI fragment. The vector was named pDVM37010. A second plasmid containing the agamous promoter in front of the m-gfp-ER reporter gene obtained from Jim Haselhoff, MRC was made as a control and was named pDVM37003.

Figure 3:
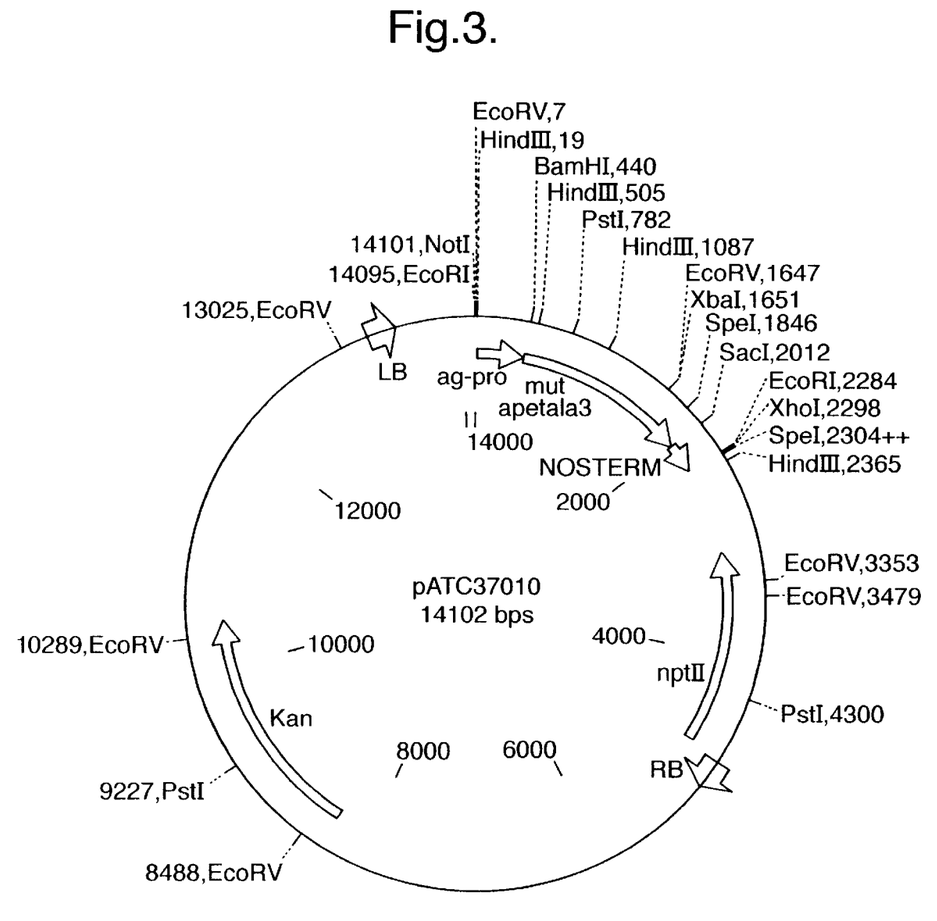
FIG. 3 shows the map for vector pATC37010 used to transform plants in accordance with the invention.
Figure 4:
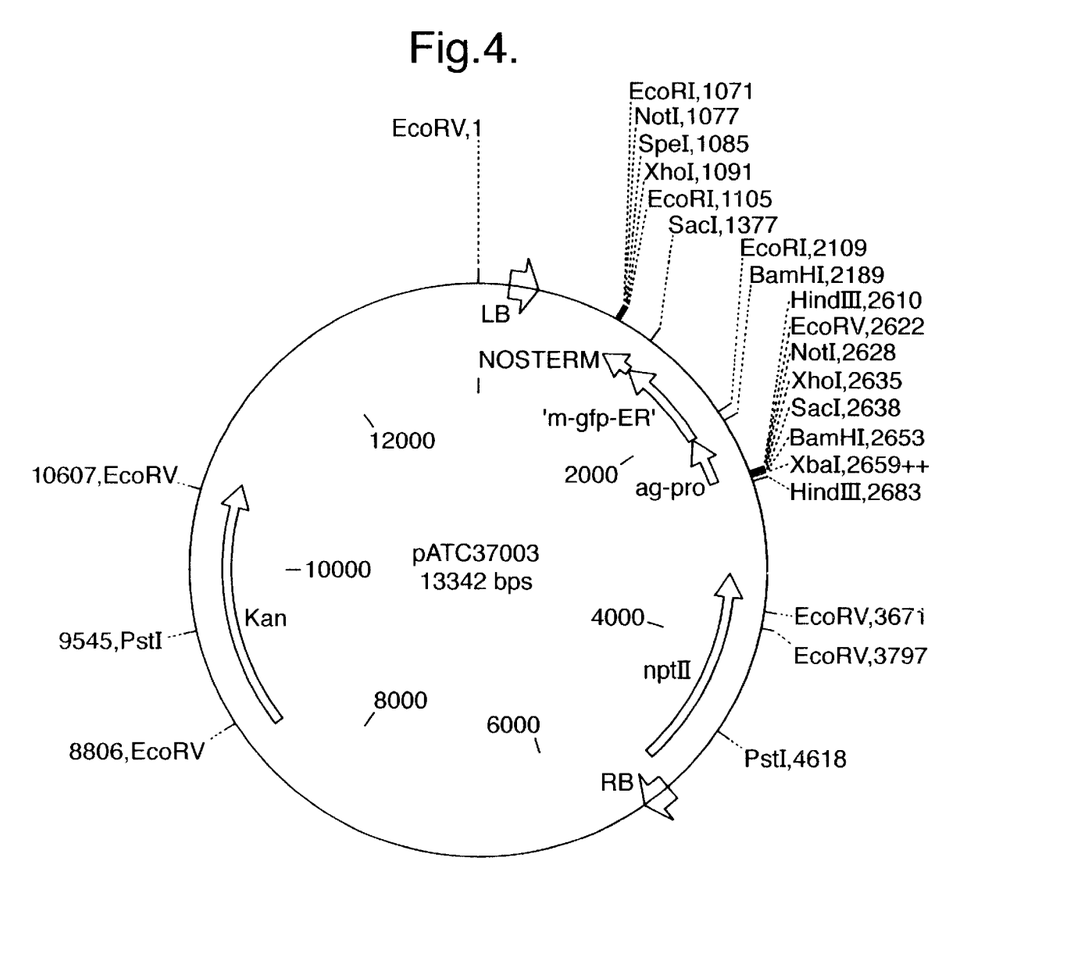
FIG. 4 shows the map for vector pATC37003, a control vector used to transform plants.
Figure 5:
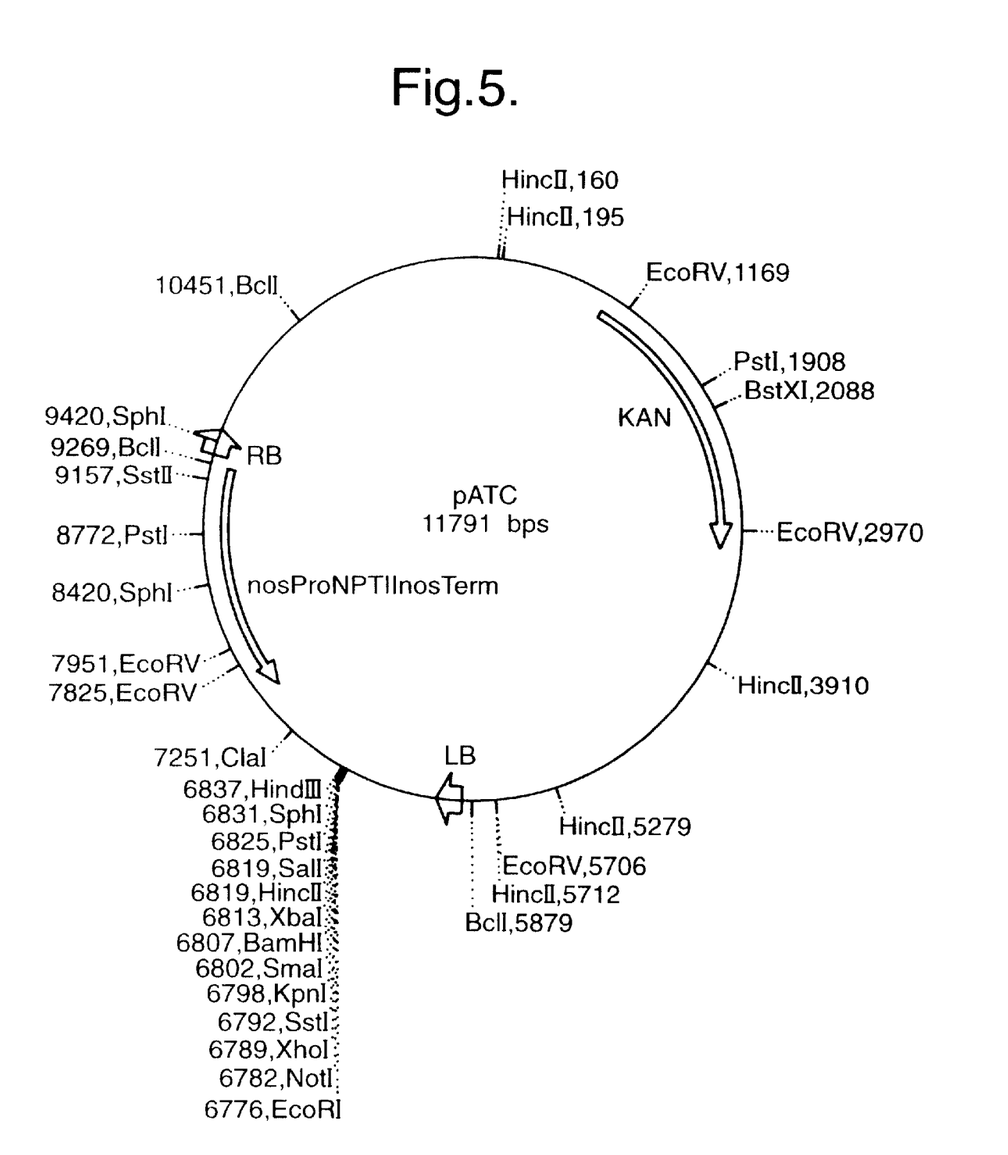
FIG. 5 shows the map for pATC into which SEQ ID NO: 5 and SEQ ID NO: 6 were ligated to produce the vectors pATC37010 and pATC37003 of FIGS. 3 and 4 respectively.

The promoter-gene fragment-terminator cassettes were excised from pDVM37010 (SEQ ID NO: 5) and pDVM37003 (SEQ ID NO: 6) as NotI restriction fragments and ligated into a pBIN19 (Bevan, M. (1984)) derived vector PATC to give plasmids pATC37010 (map shown in FIG. 3) and pATC37003 (map shown in FIG. 4). These sequences could be cloned into any other equivalent vector which has suitable restriction sites therein, i.e. NotI at each end of the cassette. The map for pATC is shown in FIG. 5. It has modified restriction sites compared with PBIN19. pATC37010 produces a co-suppression product under the control of the agamous promoter to inactivate apetala3 function in the developing stamens of the flower.

The plasmids were transferred into *Agrobacterium tumefaciens* host LBA4404 and used to transform *Arabidopsis thaliana* following the method of Bechtold et al (1993) and *Nicotiana tabacum* cv K326 using the method of Horsch et al (1985). 8 Arabidopsis plantlets transgenic for pATC37010 and 6 Arabidopsis plantlets transgenic for pATC37003 were obtained. Three sets of one hundred leaf discs were used for Nicotiana transformation for each construct. Transgenic callus growth was detected for all three sets.

The Arabidopsis plantlets were transferred into soil 10–14 days after germination and grown until flowering. The flowers exhibited no stamens, and double rose carpels.

The kanamycin resistant pATC37010 transgenic plants were further screened for the presence of the desired inserts by PCR with Taq polymerase using primers 1 and 4 following procedures known to one skilled in the art. The PCR was conducted for 40 cycles of incubation involving the steps of incubation at 94° C. for 60 seconds, 60° C. for 30 seconds and 72° C. for 140 seconds. PCR positive samples were identified by visualisation of the PCR products upon agarose gel electrophoresis following procedures known to one skilled in the art.

The control pATC37003 transgenic plants were further screened for the presence of the desired inserts by PCR with Taq polymerase using primers 1 and primer 7 following procedures known to one skilled in the art. The PCR was conducted for 40 cycles of incubation involving the steps of incubation at 94° C. for 40 seconds, 60° C. for 30 seconds and 72° C. for 140 seconds. PCR positive samples were identified by visualisation of the PCR products upon agarose gel electrophoresis following procedures known to one skilled in the art.

Primer 7 (SEQ ID NO: 7)

GAACTGGGAC CACTCCAGTG

In both cases, transgenic plants containing the appropriate construct were identified.

REFERENCES

Bechtold, N., Ellis, J., and Pelletier, G. (1993) In planta Agrobacterium mediated gene transfer by infiltration of adult *Arabidopsis thaliana* plants. C.R. Acad. Sci: Paris 316 : 1194–1199.

Bevan, M. (1984) Binary Agrobacterium vectors for plant transformation. Nuc. Acids Res. 12: 8711–8721.

Coen, E. S. and Meyerowitz, E. M. (1991). The war of the whorls: genetic interactions controlling flower development. Nature 353, 31–37.

Conkling, M. A., Cheng, C-L., Yamamoto, Y. T. and Goodman, H. M. (1990). Isolation of transcriptionally regulated root-specific genes from tobacco. Plant Physiology 93, 1203–1211.

Horsch, R. B., Fry, J. E., Hoffmann, N. L., Eichholtz, D., Rogers, S. G. and Fraley, R. T. (1985). A simple and general method for transferring genes into plants. Science 22, 1229–1231.

Jefferson, R. A., Kavanagh, T. A. and Bevan, M. W. (1987). GUS fusions: β-glucuronidase as a sensitive and versatile gene fusion marker in higher plants. EMBO, 6, 3901–3907

Opperman, C. H., Taylor, C. G. and Conkling, M. A. (1994). Root-knot nematode-directed expression of a plant root specific gene. Science 263, 221–223.

Sambrook, J., Fritsch, E. F. and Maniatis, T. (1989) Molecular Cloning—A Laboratory Manual. Second Edition, Cold Spring Harbour Laboratory Press, New York.

Thomas, C. (1996) 'PCR techniques' in 'Plant Gene Isolation: Principles and Practice'. G. D. Foster & D. Twell editors. John Wiley & Sons Ltd., pp 331–368.

Various publications are cited herein, the disclosures of which are incorporated by reference in their entireties.

Various modifications of the invention in addition to those shown and described herein will become apparent to those skilled in the art from the foregoing description and accompanying drawings. Such modifications are intended to fall within the scope of the appended claims.

What is claimed is:

1. A method of improving the specificity of gene regulation in a transformed plant comprising growing a transformed plant or a progeny thereof, wherein the transformed plant is regenerated from a plant cell that comprises a chimeric gene comprising a tissue-specific promoter and a nucleic acid seqeunce, and wherein the tissue-specific promoter transcribes the nucleic acid sequence at more than one but not all expression sites in the plant including at least one but not all of the multiple expression sites of an endogenous target gene; and wherein the tissue-specific expression of the chimeric gene regulates expression of the target gene or activity of the target gene product in the transformed plant at expression sites where the chimeric gene and the target gene are both expressed.

2. The method according to claim 1, wherein said nucleic acid sequence is a coding or a non-coding sequence.

3. The method according to claim 1, wherein the expression of said target gene is down regulated.

4. A method of improving the specificity of gene regulation in a transformed plant comprising:
   (a) introducing a chimeric gene into a cell of a plant wherein the chimeric gene comprises a tissue-specific promoter and a nucleic acid sequence, and wherein the tissue-specific promoter transcribes the nucleic acid sequence at more than one but not all expression sites in the plant including at least one but not all of the multiple expression sites of an endogenous target gene; and
   (b) regenerating a transformed plant comprising the chimeric gene from the cells,
wherein the tissue-specific expression of the chimeric gene regulates expression of the target gene or activity of the target gene product in the transformed plant at expression sites where the chimeric one and the target gene are both expressed.

5. The method according to claim 1 or 4, wherein said nucleic acid sequence is in antisense orientation.

6. The method according to any one of claims 1, 2, 3 or 4, wherein said nucleic acid sequence is in sense orientation.

7. The method according to claim 1 or 4, wherein the chimaeric gene comprises more than one nucleic acid sequences, each of which sequences, when expressed, regulates the expression of one or more target genes.

8. The method according to claim 1 or 4, wherein the promoter of the chimaeric gene is expressed in more than one overlapping expression site of the target gene.

9. The method according to claim 1, 2, 3 or 4, wherein said promoter is the KNT1 promoter or the RB7 promoter.

10. The method according to claim 9, wherein said nucleic acid sequence is in antisense orientation.

11. The method according to claim 1 or 4, wherein the promoter is inducible.

12. The method according to claim 1 or 4, wherein the mechanism whereby the nucleic acid sequence regulates expression of the target gene or activity of the target gene product is one selected from the group consisting of: antisense regulation; co-suppression; inhibition of the promoter of a target gene; inhibition of transcription; alteration of messenger RNA stability or degradation of mRNA; inhibition of translation; inhibition of a protein; alteration of protein turnover; acting as a cofactor; alteration of protein-protein interactions; and alteration of the flux through a biochemical pathway.

13. A cell having the transformation vector pBIN5002 and the accession number NCIMB 40871.

14. The transformation vector pBIN5002 contained in the cell of claim 13.

15. A construct comprising the plasmid pATC 37010 or a promoter-gene fragment-terminator cassette such as that contained in that plasmid.

16. A transformed plant produced by the method according to claim 4, or a propagule thereof.

17. The method according to claim 1 or 4, wherein the nucleic acid sequence comprises a sequence encoding an inhibitor of the target gene product.

18. The method according to claim 4, wherein the expression of said target gene is down regulated.

19. The method according to claim 4, wherein said nucleic acid sequence is a coding or a non-coding sequence.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: Other (vi) ORIGINAL SOURCE:
       (A) ORGANISM: Arabidopsis thaliana (ix) FEATURE:
       (A) NAME/KEY: Other
       (B) LOCATION: 5...10
       (D) OTHER INFORMATION: Hind III restriction site (xi) SEQUENCE DESCRIPTION: SEQ ID NO:1:

ATCGAAGCTT CTAAATGTAC TGAAAAGAAA CA                              32

(2) INFORMATION FOR SEQ ID NO:2:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: Other (iv) ANTI-SENSE: YES (vi) ORIGINAL SOURCE:
       (A) ORGANISM: Arabidopsis thaliana (ix) FEATURE:
       (A) NAME/KEY: Other
       (B) LOCATION: 5...10
       (D) OTHER INFORMATION: Bam HI restriction site (xi) SEQUENCE DESCRIPTION: SEQ ID NO:2:

ACTGGGATCC GAAAATGGAA GGTAAGGTTG TGC                             33

(2) INFORMATION FOR SEQ ID NO:3:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: Other (ix) FEATURE:
       (A) NAME/KEY: Other
       (B) LOCATION: 5...10
       (D) OTHER INFORMATION: Bam HI restriction site
       (A) NAME/KEY: Other
       (B) LOCATION: 11...13
       (D) OTHER INFORMATION: start codon
       (A) NAME/KEY: Other
       (B) LOCATION: 14...0
       (D) OTHER INFORMATION: deliberate base change from
           A to G (xi) SEQUENCE DESCRIPTION: SEQ ID NO:3:

ATCGGGATCC ATGGGCTCAC GGTTTTGTGT GA                                32

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (iv) ANTI-SENSE: YES (ix) FEATURE:
        (A) NAME/KEY: Other
        (B) LOCATION: 5...10
        (D) OTHER INFORMATION: Sac I restriction site (xi) SEQUENCE DESCRIPTION: SEQ ID NO:4:

ATCGGAGCTC TTATTCAAGA AGATGGAAGG TAATGA                            36

(2) INFORMATION FOR SEQ ID NO:5:

(i) SEQUENCE CHARACTERISTICS:
        (A) LENGTH: 2319 base pairs
        (B) TYPE: nucleic acid
        (C) STRANDEDNESS: double
        (D) TOPOLOGY: both (ii) MOLECULE TYPE: Other (vi) ORIGINAL SOURCE:
        (A) ORGANISM: Arabidopsis thaliana
        (B) STRAIN: Landsberg (ix) FEATURE:
        (A) NAME/KEY: Other
        (B) LOCATION: 26...441
        (D) OTHER INFORMATION: promoter- Arabidopsis agamous
            (GenBank ATAGAMSG)
        (A) NAME/KEY: Other
        (B) LOCATION: 448...2013
        (D) OTHER INFORMATION: coding sequence- Arabidopsis
            apetala3 (GenBank ATHPETALA)
        (A) NAME/KEY: Other
        (B) LOCATION: 2020...2286
        (D) OTHER INFORMATION: Nos terminator (xi) SEQUENCE DESCRIPTION: SEQ ID NO:5:

GCGGCCGCGA TATCGTCGAC AAGCTTCTAA ATGTACTGAA AAGAAACACC AGTTTAATTA    60

ATTATACTTT CCTCACATAT AACTATCAAC CAAGTACAAA ACTTTTGTCA ATTCTCAAAA   120

TCAACTTTCA CCACATAATT ATCTAACATG TGTATGTTCC AAAACCAGTT TAAATGAATT   180

ACTTTTCAGA AAATACATGT ATATTAACTC TATCTAATAA AGAAGAAACA CATACTTATC   240

TCATAGATTC CATTCATAAA ACTATGCTTT AGTGAGTAAG AAAACCAGTA ATCAAACACA   300

AATTGACAAG ACACTATATG GATGTAAAAA GTGGGGAAAA TATGGTGATA AATAGTAGAG   360

AAAATTAAAA AGAAAAAATA ATATTCCTTT ATAAATGTAT ATACCCATCT CTTCACCAGC   420

ACAACCTTAC CTTCCATTTT CGGATCCATG GGCTCACGGT TTTGTGTGAT GCTAGGGTTT   480

CGATTATCAT GTTCTCTAGC TCCAACAAGC TTCATGAGTA TATCAGCCCT AACACCACGT   540

ACACCATCTC TCTAAACACC ACTCTTAAAT TAAGCTAATT GAGTTGCTTT GTTTTCTTAT   600

AATTAACCAC TACTTTTTTG GTGATTTTGT TGGTTATAGA ACGAAGGAGA TCGTAGATCT   660

GTACCAAACT ATTTCTGATG TCGATGTTTG GGCCACTCAA TATGAGGTTT TTTTCCTTCT   720

```
TAGATCTTTC TTCTTCTTCT TGATATGTGT TTCGCTGGTT GGTTAAATTC TTGATGCGTT      780

TTGCTGCAGC GAATGCAAGA AACCAAGAGG AAACTGTTGG AGACAAATAG AAATCTCCGG      840

ACTCAGATCA AGTATTTGTT TCTTCTCTCT TCTCTTAGAT GAGGAGTTTT ACTAAAAAAA      900

ATGAGTACGG AAATATACAT ATTTTTAAAA TTGTAGGCAG AGGCTAGGTG AGTGTTTGGA      960

CGAGCTTGAC ATTCAGGAGC TGCGTCGTCT TGAGGATGAA ATGGAAAACA CTTTCAAACT     1020

CGTTCGCGAG CGCAAGGTTC TCTTCATACT TTTCCCTTAC CTAGGGTTTC AATTAATCCT     1080

ATATACCCAA GCTTCAGTTT TGAATTGAAT TATTAAAAAA TGAATTTTAT TGTTGTATAT     1140

ATGTTTTAGA AAAGAAACA TTTTGTTTAC TGTTGGATAA TATATGTTAA TTGTATTGTA     1200

CTGTACAGTT CAAATCTCTT GGGAATCAGA TCGAGACCAC AAGAAAAAG GTCACATCTT      1260

CTATGTCCAC TCACTTTTCC ATTTTATCAT ATTTATTTGT CTCAACAATT TTGTGACAAT     1320

TGAATTTATC AACTTACTAA AACTGTTGAT AACACTTTTC TTGGACAATT ATATTTGTGT     1380

GTGTGTGTGT GTGTGTTTAA GCTAATGGAT AAAGAAAATA CCAAGTATAC TATATAGTGA     1440

TGTCATAATA ACTTGGGTAT ATATCTTCAT AATTTTTTTG GGTGGGAATA TTTCTTCATA     1500

ATTTCTCTTG TGGTTTACAC AATTGCAGAA CAAAGTCAA CAGGACATAC AAAAGAATCT      1560

CATACATGAG CTGGTAATAT CTCTTTCTGT TTTTCTCAAA TGTTGGTTTA GGCATAATAC     1620

ATTCATGGAA TACGGAGCCA GTTAAAAAGA TATCTAGAAA TGTAGTGTAG ATTGATCAGT     1680

CACTCTTATG TTTTCTTGTG ATTCTCTTAT CGAAATATCT CCTAGTTAAA TCATATATCA     1740

AATGTCATGT CATTTCGAAT TAATAATATT GGTTTTAGTT ATGTGGAATA TGGCTTAAAA     1800

CATGTTTTGG TGAATTAGGA ACTAAGAGCT GAAGATCCTC ACTATGGACT AGTAGACAAT     1860

GGAGGAGATT ACGACTCAGT TCTTGGATAC CAAATCGAAG GGTCACGTCG TTACGCTCTT     1920

CGTTTCCACC AGAACCATCA CCACTATTAC CCCAACCATG GCCTTCATGC ACCCTCTGCC     1980

TCTGACATCA TTACCTTCCA TCTTCTTGAA TAAGAGCTCG AATTTCACCC GATCGTTCAA     2040

ACATTTGGCA ATAAAGTTTC TTAAGATTGA ATCCTGTTGC CGGTCTTGCG ATGATTATCA     2100

TATAATTTCT GTTGAATTAC GTTAAGCATG TAATAATTAA CATGTAATGC ATGACGTTAT     2160

TTATGAGATG GGTTTTTATG ATTAGAGTCC CGCAATTATA CATTTAATAC GCGATAGAAA     2220

ACAAAATTAT GCGCGCAAAC TAGGATAAAT TATCGCGCGC GGTGTCATCT ATGTTACTAG     2280

ATCGGGAATT CTGTTTAAAC TCGAGACTAG TGCGGCCGC                            2319

(2) INFORMATION FOR SEQ ID NO:6:

(i) SEQUENCE CHARACTERISTICS:
        (A) LENGTH: 1559 base pairs
        (B) TYPE: nucleic acid
        (C) STRANDEDNESS: double
        (D) TOPOLOGY: both (ii) MOLECULE TYPE: Other (ix) FEATURE:
        (A) NAME/KEY: Other
        (B) LOCATION: 26...441
        (D) OTHER INFORMATION: promoter- Arabidopsis agamous
        (GenBank ATAGAMSG)
        (A) NAME/KEY: Other
        (B) LOCATION: 443...1258
        (D) OTHER INFORMATION: coding sequence- green fluorescent
            protein
        (A) NAME/KEY: Other
        (B) LOCATION: 1260...1526
        (D) OTHER INFORMATION: Nos terminator (xi) SEQUENCE DESCRIPTION: SEQ ID NO:6:
```

```
GCGGCCGCGA TATCGTCGAC AAGCTTCTAA ATGTACTGAA AAGAAACACC AGTTTAATTA      60

ATTATACTTT CCTCACATAT AACTATCAAC CAAGTACAAA ACTTTTGTCA ATTCTCAAAA     120

TCAACTTTCA CCACATAATT ATCTAACATG TGTATGTTCC AAAACCAGTT TAAATGAATT     180

ACTTTTCAGA AAATACATGT ATATTAACTC TATCTAATAA AGAAGAAACA CATACTTATC     240

TCATAGATTC CATTCATAAA ACTATGCTTT AGTGAGTAAG AAAACCAGTA ATCAAACACA     300

AATTGACAAG ACACTATATG GATGTAAAAA GTGGGGAAAA TATGGTGATA AATAGTAGAG     360

AAAATTAAAA AGAAAAAATA ATATTCCTTT ATAAATGTAT ATACCCATCT CTTCACCAGC     420

ACAACCTTAC CTTCCATTTT CGGATCCAAG GAGATATAAC AATGAAGACT AATCTTTTTC     480

TCTTTCTCAT CTTTTCACTT CTCCTATCAT TATCCTCGGC CGAATTCAGT AAAGGAGAAG     540

AACTTTTCAC TGGAGTTGTC CCAATTCTTG TTGAATTAGA TGGTGATGTT AATGGGCACA     600

AATTTTCTGT CAGTGGAGAG GGTGAAGGTG ATGCAACATA CGGAAAACTT ACCCTTAAAT     660

TTATTTGCAC TACTGGAAAA CTACCTGTTC CATGGCCAAC ACTTGTCACT ACTTTCTCTT     720

ATGGTGTTCA ATGCTTTTCA AGATACCCAG ATCATATGAA GCGGCACGAC TTCTTCAAGA     780

GCGCCATGCC TGAGGGATAC GTGCAGGAGA GGACCATCTT CTTCAAGGAC GACGGGAACT     840

ACAAGACACG TGCTGAAGTC AAGTTTGAGG GAGACACCCT CGTCAACAGG ATCGAGCTTA     900

AGGGAATCGA TTTCAAGGAG GACGGAAACA TCCTCGGCCA CAAGTTGGAA TACAACTACA     960

ACTCCCACAA CGTATACATC ATGGCCGACA AGCAAAAGAA CGGCATCAAA GCCAACTTCA    1020

AGACCCGCCA CAACATCGAA GACGGCGGCG TGCAACTAGC TGATCATTAT CAACAAAATA    1080

CTCCAATTGG CGATGGCCCT GTCCTTTTAC CAGACAACCA TTACCTGTCC ACACAATCTG    1140

CCCTTTCGAA AGATCCCAAC GAAAAGAGAG ACCACATGGT CCTTCTTGAG TTTGTAACAG    1200

CTGCTGGGAT TACACATGGC ATGGATGAAC TATACAAACA TGATGAGCTT TAAGAGCTCG    1260

AATTTCACCC GATCGTTCAA ACATTTGGCA ATAAAGTTTC TTAAGATTGA ATCCTGTTGC    1320

CGGTCTTGCG ATGATTATCA TATAATTTCT GTTGAATTAC GTTAAGCATG TAATAATTAA    1380

CATGTAATGC ATGACGTTAT TTATGAGATG GGTTTTTATG ATTAGAGTCC CGCAATTATA    1440

CATTTAATAC GCGATAGAAA ACAAAATTAT GCGCGCAAAC TAGGATAAAT TATCGCGCGC    1500

GGTGTCATCT ATGTTACTAG ATCGGGAATT CTGTTTAAAC TCGAGACTAG TGCGGCCGC     1559
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: Other     (iv) ANTI-SENSE: YES     (vi) ORIGINAL SOURCE:
        (A) ORGANISM: Aequorea victoria     (xi) SEQUENCE DESCRIPTION: SEQ ID NO:7:

```
GAACTGGGAC CACTCCAGTG                                                  20
```